United States Patent [19]

Lucero

[11] Patent Number: 4,883,505
[45] Date of Patent: Nov. 28, 1989

[54] METHODS AND APPARATUS FOR ATMOSPHERIC SAMPLING AND ANALYSIS OF TRACE CONTAMINANTS

[75] Inventor: Daniel P. Lucero, Triangle, Va.
[73] Assignee: IIT Research Institute, Chicago, Ill.
[21] Appl. No.: 223,283
[22] Filed: Jul. 22, 1988
[51] Int. Cl.[4] ............................................. B01D 53/30
[52] U.S. Cl. .......................................... 55/84; 55/270; 73/864.81; 73/863.21; 73/863.11
[58] Field of Search ................. 55/270, 84; 73/864.81, 73/863.21, 863.11

[56] References Cited

U.S. PATENT DOCUMENTS

| | | | |
|---|---|---|---|
| 3,201,993 | 8/1965 | Moody et al. | 73/863.11 |
| 3,999,963 | 12/1976 | Ririe | 55/270 |
| 4,479,379 | 10/1984 | Tarcy | 55/270 |

Primary Examiner—Bernard Nozick
Attorney, Agent, or Firm—Fitch, Even, Tabin & Flannery

[57] ABSTRACT

This invention relates to a method and device for continuously removing and concentrating specific molecules or substances from a gas stream and depositing such molecules or substances in a liquid film stream in a controlled and quantitative fashion. The device includes a hollow tetrafluoroethylene tube or a hollow tube having an inner surface coating of tetrafluoroethylene. The inner surface of the tube is etched by means of a chemical etching agent. An inlet/injector is attached to the outer circumference or inlet, circumferential face of the tube. The inlet/injector has liquid dispersion ports uniformly distributed around the circumference of the processor tube whereby a surfactant containing liquid may be uniformly dispersed from the inlet/injector onto the inner wall of the processor tube where it may flow, in a thin film manner, from the inlet of the tube to the outlet of the tube. The inlet/injector also has a gas injection port whereby a gas containing the molecules or substances sought to be removed and concentrated can simultaneously be injected into the top hollow portion of the tube. An outlet cap is attached to the outer circumference or outlet circumferential face of the tube. The outlet cap has a liquid collection well with a port or other means whereby the liquid flowing down the inner wall of the tube can be collected and transported to an analyzer. The outlet cap also has a gas port whereby the sample gas undergoing analysis can be removed from the tube and vented, treated or otherwise disposed of.

13 Claims, 3 Drawing Sheets

METHODS AND APPARATUS FOR ATMOSPHERIC SAMPLING AND ANALYSIS OF TRACE CONTAMINANTS

BACKGROUND OF THE INVENTION

This invention relates to methods and apparatus for atmospheric sampling and analysis of trace contaminants, and more particularly, the invention relates to such methods and apparatus which utilize gas-phase preconcentration interface systems.

The rapid and accurate monitoring of atmospheric contaminants, such as hazardous waste incinerator flue gas streams, is an important and necessary aspect of air quality control programs. Such hazardous trace materials may be formed during the incineration of either hazardous or non-hazardous materials, or may pass through the combustion apparatus unchanged as a result of incomplete destruction of a hazardous material by the incineration process.

However, despite the advances made in the detection of substances in gas streams, frequent or continuous monitoring of such streams for highly toxic substances has not achieved the desired level of utility because of the difficulty encountered in obtaining samples, the laborious techniques frequently utilized to sample extremely dilute gas streams for a sufficient length of time to obtain a sample concentration sufficient for analysis, and the length of time necessary in certain procedures to prepare the sample for analysis. As a consequence of these difficulties, many exhaust or stack gas streams, such as those coming from municipal, industrial or hazardous waste incinerators, are only monitored periodically for the presence of toxic substances. For example, a hazardous waste incinerator may monitor for dioxin at certification and recertification (2-4 years) only. On the basis of this infrequent monitoring, the incinerator operator will make periodic adjustments in an effort to prevent toxic substance emissions from exceeding specifications, but system, feedstock, or process changes between such adjustments may adversely affect emission control. If, however, more rapid and less cumbersome methods of analysis were available, the incinerator operator could make more frequent adjustments.

While many systems have been used to sample and concentrate the components of a gas stream, the most commonly used systems are a bubbler or scrubber device where the gas is passed through a counter-current or stationary liquid, a solid sorbent such as charcoal, a suitable polymer and molecular sieves. Such methods, however, require additional steps to prepare the samples for analysis by the analytical instrument. Methods and apparatus for rapidly providing a reliably high degree of concentration of atmospheric contaminants in a sample stream which can be directly injected into an analytical instrument without requiring additional sample preparation steps would be desirable.

Efforts to monitor the content of a specific hazardous component (3-Quinuclidinyl benziloute or "BZ") in the flue gas of an incinerator being utilized to destroy the hazardous material are reported in "BezeTrog: An Effluent Sampling System for the BZ Incinerator Stack", for The Aerospace Corporation under Government Contract No. TOR-0084 (4712)-1 (1986); and "Theoretical Aspects of a Liquid Chromatographic Gas-Phase Interface", *J. Chromatographic Science*, Vol. 23, pp. 293-303 (1985). These publications describe a wetted-wall device in which the collection and concentration of trace quantities of BZ in incinerator flue gas was carried out in a concentration module comprising a small bore hollow cylindrical fluorocarbon polymer (Teflon) tube to achieve 8,000-10,000 fold concentration. While such a concentration increase is adequate for many substances which are present in a gas stream in the parts-per-million (ppm) range, further concentration is desirable, particularly when the hazardous substance is in the part-per-billion (ppb) range. In this regard, concentration increases to a range of at least 70,000-80,000 times the sample gas concentration of the hazardous trace substances would be desirable for rapid quantitative analysis of hazardous materials such as BZ in incinerator flue gases.

DESCRIPTION OF THE INVENTION

Generally in accordance with the present invention, methods and apparatus are provided for atmospheric sampling and preconcentration of trace hazardous substances in a gas stream. In accordance with apparatus aspects of the invention, such apparatus may comprise a sample probe for receiving a gas sample to be analyzed, and a gas sample processor conduit having an inlet end and a discharge end in fluidic connection with the sample probe at said inlet end of the sample processor conduit. The conduit has a length of at least about 100 inches, a cross-sectional area in the range of from about 0.15 square inch to about 0.30 square inch, and has a substantially inert hydrophylic inner absorbent liquid contacting surface.

The apparatus further comprises absorbant pump means for continuously introducing a predetermined quantity of absorbant liquid comprising water and a surfactant into the sample processor at the inlet end of the probe to function as a hazardous substance an absorbant. The provision of the hydrophylic inner surface of the gas sample processor conduit and the provision of a surfactant-containing absorbant liquid are important features which provide for effective reproducible and uniform preconcentration of contaminant substances in the absorbant liquid from a gas sample conducted through the gas sample processor conduit.

The apparatus further comprises separation means in fluidic connection with the discharge end of the gas sample processor for separating a gas sample stream discharged from the discharge end of the gas sample processor from an absorbant liquid discharged from the discharge end of the gas sample processor, to provide a liquid preconcentrated sample stream and a contaminant-depleted gas sample stream, gas drying means in fluidic connection with the separation means for drying a contaminant-depleted gas sample stream from the separation means, and vacuum pump means for withdrawing a gas sample stream from the sample probe through the gas sample processor conduit, the gas-liquid separation means, and the gas drying means at a rate in the range of from about 150 to 260 liters per minute. The rate of flow of the gas will, of course, be decreased in the dryer by the amount of water vapor removal. The vacuum pump should best not exceed about 0.1 atmosphere of vacuum in order to prevent mist formation within the gas sample processor conduit.

The sample processor of this invention serves to remove and concentrate gas-phase sample molecules in a liquid medium that can be directly injected into an analyzer such as a liquid chromatograph or colorimetric analyzer without the necessity of laborious and time-consuming sample preparation, and may be used in a field analysis device of an on-site device. The sample processor of this invention is incorporated in a gas sampling unit that can be used to sample ambient air, exhaust systems, incinerator stacks and the like for toxic and hazardous substances such as dioxin; 2,4,5-T; BZ; endrin oxamyl, and crimidine. Sample molecules are concentrated in a thin layer flowing liquid stream by extraction from a co-current, turbulent flow gas stream. The liquid stream may be directly injected into a detector or analyzer to determine the presence and concentration of the sample.

This invention relates to a device for continuously removing and concentrating specific molecules or substances from a gas stream and depositing such molecules or substances in a liquid film stream in a controlled and quantitative fashion, the device comprising (a) a hollow Teflon tube or a hollow tube having an inner surface coating of Teflon, said inner surface being etched by means of a chemical etching agent; (b) an inlet/injector attached to the outer circumference or inlet, circumferential face of the tube by means of screw threads, clips, welding, glueing or other such means, the inlet/injector having liquid dispersion ports uniformly distributed around the circumference of the processor tube whereby a surfactant containing liquid, entering into the cap from an external source, may be uniformly dispersed from the inlet/injector onto the inner wall of the processor tube where it may flow, in a thin film manner, from the inlet of the tube to the outlet of the tube, and the inlet/injector also having a gas injection port whereby a gas containing the molecules or substances sought to be removed and concentrated can simultaneously be injected into the top hollow portion of the tube; and (c) an outlet cap attached to the outer circumference or outlet circumferential face of the tube by means of screw threads, clips, welding, glueing or other such holding means, the outlet cap having a liquid collection well with a port or other means whereby the liquid flowing down the inner wall of the tube can be collected and transported to an analyzer, and the outlet also having a gas port whereby the sample gas undergoing analysis can be removed from the tube and vented, treated or otherwise disposed of.

This invention also relates to a method for removing and concentrating specific molecules or substances from a gas stream and depositing such molecules or substances in a liquid film stream in a controlled and uniform manner, such method comprising the steps of: (a) sampling a gas stream by means of a gas probe inserted in the gas stream and transporting the sample through and a heated gas transport line to the inlet portion of a hollow tube having an inner diameter of from about 0.35 to about 0.625 inch and a hydrophilic inner surface; (b) dispersing a surfactant containing liquid uniformly and circumferentially on the inner wall surface of the hollow tube or hollow coated tube at a rate in the range of from about 6 to about 11 milliliters per minute by means of dispersing ports uniformly placed in the inlet/injector portion of said tube, the surfactant containing liquid having been delivered to the dispersion ports at a controlled rate from a liquid reservoir by a liquid pump, a solenoid controlled valve and a metering valve; (c) removing the molecules or substances to be analyzed from the gas stream by means of contact of the gas stream with the liquid stream whereby the molecules or substances to be analyzed are moved from the gas stream and concentrated in the liquid stream at the gas-liquid interface; (d) collecting the liquid containing the concentrated molecules or substance in the liquid collection well located circumferentially in the outlet portion of the sample processing tube, the outlet being attached to the bottom outer circumference or circumferential face of the tube by means of screw threads, clips, welding, glueing or other such holding means, and the outlet having a liquid port leading from the liquid well through the outlet whereby the liquid collected in the well can be removed, and a gas port whereby the gas sample which has been contacted with the liquid sample is passed through a shell-and-tube type drying train wherein the tubes are fiber membranes permeable to water in which the sample gas containing water from the flue and the sample processor passes through the center of the fiber and a drying gas such as dry air passes between the shell of the dryer and the outer surface of the membrane tubes prior to passage through a vacuum pump which serves to both pull the untreated gas sample through the unit from the flue via the sample probe and exhaust the processed gas sample back to the flue; and (e) a liquid sample line and a liquid sample pump which transports the liquid containing the substance extracted from the gas sample to the wet chemical analyzer.

The device and method of this invention may desirably utilize a ⅜ inch sample processing tube having an inner diameter of about ½ inch, a liquid flow rate into the sample processing tube in the range of about 7–10 ml/min and a gas sample flow rate through the tube in the range of about 200–300 l/min, and preferably in the range of about 240–260 l/min. In addition, in the present invention, the working surface or inner wall of the sample processing tube is etched by means of a chemical etching agent to render the entire inner surface hydrophilic. The liquid which is used to extract the substances from the gas stream contains a surfactant, and the sample processor is heated to a temperature above the dew point of the extracting liquid and the substance sought to be extracted from the gas stream. The combined effect resulting from a high gas throughput and lo liquid throughput is that the substance is concentrated by a factor in the range of 50,000–80,000 in the liquid phase as compared to its concentration in the gas phase.

In the present invention, it has been found that etching the working surface or inner wall of the sample processor enables the extracting liquid to more uniformly coat the surface of the wall in a thin film manner. While sample processor tubes may be made of metal, plastics or polymers such as fluorocarbons or chlorofluorocarbons like Teflon, polyethylene, polypropylene, polyphenylene oxide, polyphenylene sulfide, polyamides, polyamines, polyesters and metal with an inner coating of such polymers and plastics, the preferred sample processor tubes are made of substantially inert polyfluorocarbons such as Teflon, or are made of metal having an inner surface coating of Teflon or Teflon-like material. The working surface or inner wall of the tubes are etched by means of a chemical etching agent such as sodium or potassium in liquid ammonia, sodium napthenate or other etching agents known in the art, which are capable of substituting hydroxyl or other hydrophylic groups for fluorine groups at the inner surface of the gas sample processor conduit. In the case of metal tubes, the etching serves to remove all processing oils and other substances which might repel the extracting liquid as well as providing a roughened surface whereby the liquid can adhere to the wall of the tube. When plastics or polymers are used as the tube material or as a coating on the inner wall of a metal tube, the etching not only removes any substances which may repel the extracting liquid, but also performs a chemical reaction on the surface of the polymer or plastic whereby a polymer chain may be broken or an atom replaced by another atom resulting in a surface which has a greater affinity for the extracting liquid. For example, if the tube is a polyamide or a polyamine, a carbon-nitrogen bond may be broken to provide an amine function and an acid function which will more readily interact with the extracting liquid. If a fluorocarbon or fluorocarbon coated tube is used as the sample processor, a fluorine atom (or a chlorine atom in the case of chlorofluorocarbons) may be replaced with another atom or molecular species which will more readily interact with the extracting liquid. It was observed that in etched tubes, the working surface or inner wall of the sample processing tube was uniformly coated with the extracting liquid whereas an unetched wall was subject to uneven coating.

The thin film flow of the extracting liquid can also be enhanced by the use of a non-ionic surfactant. In particular, the thin film flow of the extracting liquid can be enhanced by a non-ionic surfactant when the extracting liquid is water. The specific type of surfactant used in the invention is not critical except that the surfactant should not interfere with the substance or substances which are being analyzed. The surfactant serves to increase the "wetting power" of the extracting liquid and thereby facilitates the liquid flowing through the tube in a thin film manner.

It is important to the accuracy and reproducibility of the method of the invention that the temperature of the sample processing tube be controlled at a temperature which is above the dew point of either the extracting liquid or the substance being analyzed. If the temperature is not so controlled, microscopic liquid droplets may form in the gas stream onto which the substance being analyzed may be adsorbed and carried out of the sample processing tube in the gas stream instead of the liquid streeam. Liquid condensation on dust particles carried into the sample processor from the flue may cause a similar effect. Further, if the substance being analyzed is a solid at ambient temperature, it could condense within the sample tube and be carried in the gas stream as a "snow" instead of being absorbed into the liquid sample stream. The ocurrence of any of these three events will lead to erroneous results from the wet chemical analyzer. The analytical results will be lower than the true concentration in the flue and could thus lead to potentially harmful emission from the flue.

Figure 1:
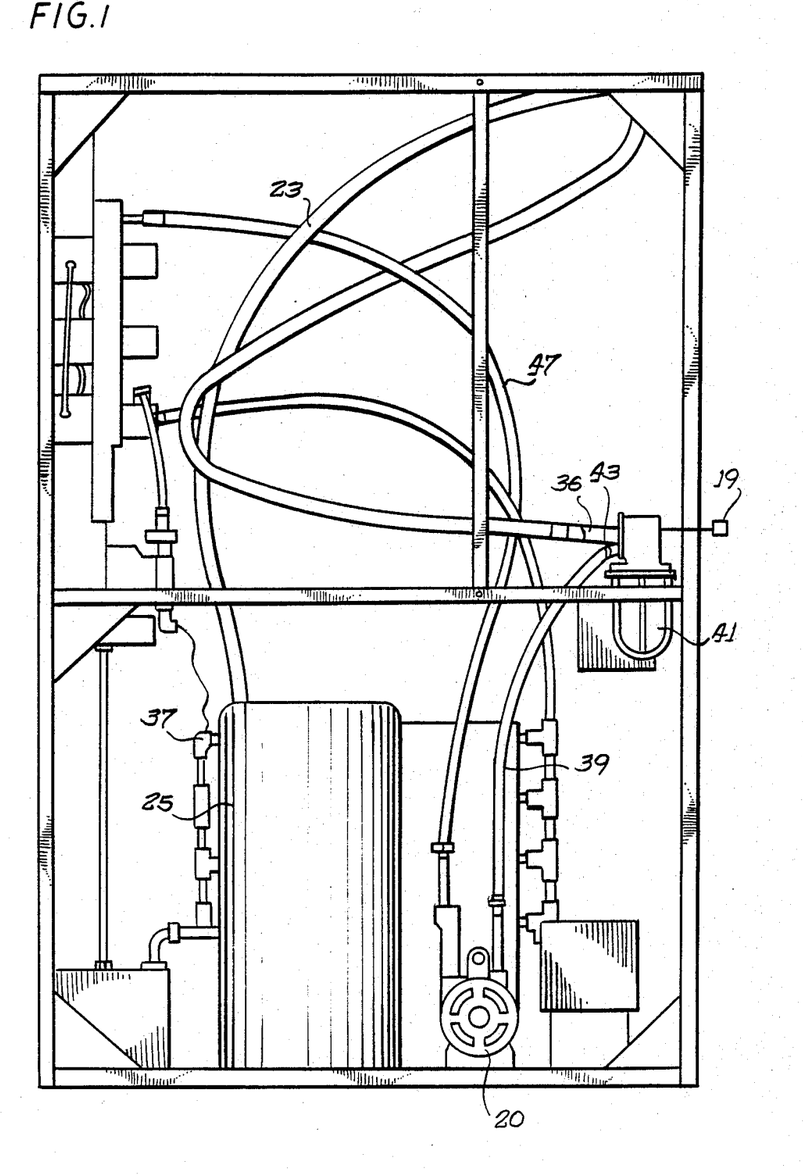
FIG. 1 is an illustration of an embodiment of gas sampling and hazardous substance preconcentration apparatus in accordance with the present invention.
Figure 2:
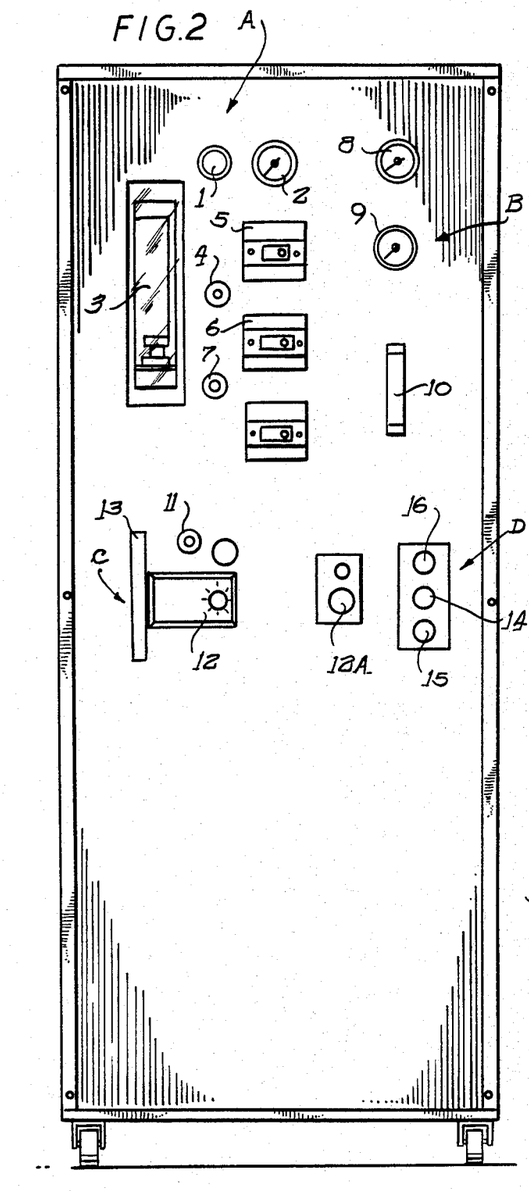
FIG. 2 is an illustration of the control panel of the preconcentration apparatus of FIG. 1.

Illustrated in FIGS. 1-4 and described in the reports attached hereto and incorporated hereto as Appendix A, is an embodiment of gas sampling and contaminant preconcentration apparatus together with a colorimetric analyzer. FIGS. 1 and 2 illustrate the apparatus including its control panel. Section A consists of the sample processor controls which are the sample gas flow adjust control 1, a vacuum gauge 2, a gas flow rotometer 3, a sample processor heater control switch 4, a gas transport line temperature limiter/indicator 5, a sample processor temperature limiter/indicator 6, and vacuum pump control switch 7. Section B, the dryer section of the control panel consists of a temperature indicator 8, a pressure gauge 9 and an air flow rotometer 10. The liquid control section, Section C, consists of a liquid pump control 11 gas sample pump control 12, an injector pump control 12A to regulate the injection of the liquid into the sample processing tube, and an injector liquid flow rotometer 13. The power controls in Section D consist of power ON 14 and OFF 15 switches and a power-on indicator light 16.

Figure 3:
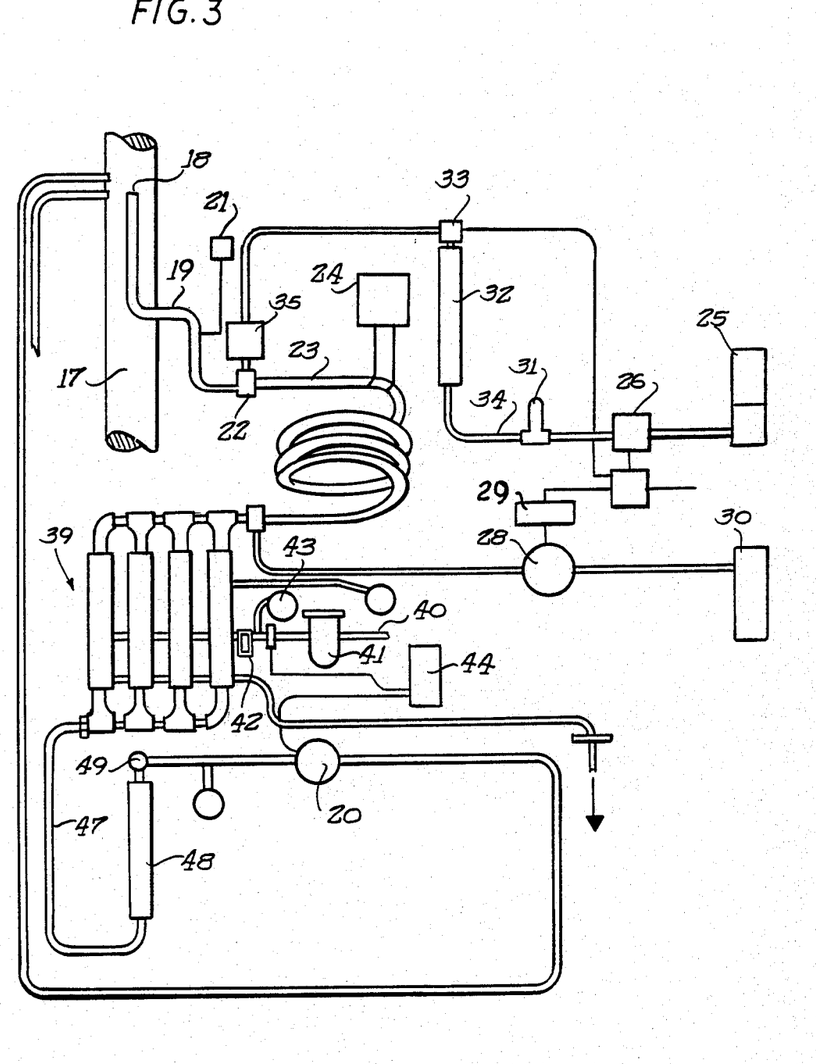
FIG. 3 is a semi-schematic illustration of the preconcentration apparatus of FIG. 1, together with a colorimetric detection apparatus for continuously monitoring a hazardous substance in incinerator flue gas.

FIG. 3 is a schematic illustration of the gas sampling and processing apparatus, including the sample processor, used to practice the method of this invention. A sample probe 18 consisting of a perforated cylinder attached to a gas transport line 19 is placed in a flue or stack containing the incineration or waste gases to be analyzed. The sample is drawn into the sample section by suction supplied by vacuum pump 20. The transport line 19 is heated by means of heating wire or tape wrapped around said transport line. The temperature of the transport line is set and controlled by means of temperature controller 21. The gas sample is transported to the inlet side 22 of the sample processing tube 23. The sample processing tube 23 is maintained at a desired operating temperature by means of heating wire, heating tape or concentric outer heating tube 54 surrounding the sample processing tube and controlled by temperature controller 24. The molecules or substances in the sample gas stream are concentrated in a liquid in the sample processor tube 23. The liquid is pumped from a liquid reservoir 25 by means of a liquid feed pump 26 controlled through liquid transport line 34, pulse suppressor 31, fluid flow meter 32, solenoid valve 33 controlled by on/off switch 27 and metering valve 35 into the injector 36 located in the inlet 22 of the sample processor 23 where the liquid is uniformly dispersed circumferentially on the inner wall of the sample processing tube 23. The gas and liquid in sample processor 23 flow concurrently through the sample processor to the outlet 37 which also serves as a stream splitter to separate the liquid and gas streams. The liquid stream is collected within the outlet 37 in a well 56 formed by the gas outlet tube 57 and the inner wall of the sample processor 52. The liquid collected within said well 56 is removed through a port 58 in the well 56 through the liquid transport line 38 and liquid sample pump 28 controlled by sample pump controller 29 to wet the chemical analyzer 30.

The gas sample from stream splitter 37 passes through a bank of drying tubes 39 that are filled with bundles of fiber membranes which are very permeable to water vapor, but less permeable to other molecules. The moisture laden sample gas from stream splitter 37 passes through the interior of the fiber membranes and dry air is passed between the outer surface of the fiber membranes and the shell of the drying tube by means of dry air line 40. The dry air is filtered by means of air filter 41 to remove particles, oil mist and other substances which may plug the pores of the fiber membranes. The supply of dry air is monitored by means of flow meter 42 and is controlled by solenoid valve 43 and switch 44 which switch also controls vacuum pump 20. The drying air exits the drying tubes through line 45 and manifold 46, and is vented in flue 17. The moisture-free gas sample exits the drying tubes through line 47, flow meter 48, control valve 49 and vacuum pump 20 before being vented in flue 17.

Figure 4:
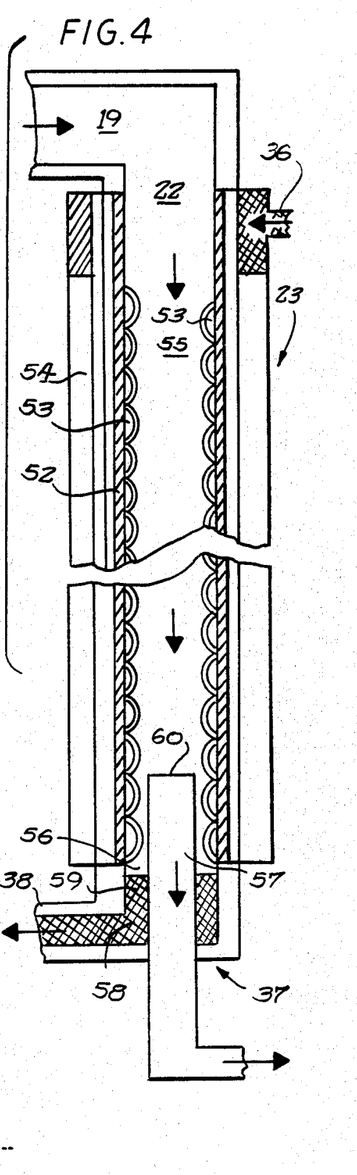
FIG. 4 is an illustration of the surface-treated sample processor tube of the apparatus of FIG. 1.

FIG. 4 is a drawing of the sample processing tube portion of the unit, expanded to show the interior details of the tube. The gas sample coming from flue 17 via transport line 19 passes through inlet 22 into the central portion 55 of the sample processing tube 23 where it is contacted with the liquid thin film 53, forming by means of liquid injector 36, flowing along the interior wall 52 of the tube. The substance to be analyzed in the gas sample is extracted from the sample gas in central portion 55 at the gas liquid interface to form liquid 59 which contains the substance therein. The liquid containing the substance enters the outlet 37 of the tube which is also a stream splitter that separates the gas and the liquid phases. The liquid collects in well 56 formed by the inner wall 52 of the sample processor tube and the gas outlet tube 59. The liquid in well 56 is removed through port 57 and liquid transport line 38 to the wet chemical analyzer. The gas stream exits through outlet 60 to dryer tubes 39. A portion of the liquid (e.g., from about 25 percent to about 75 percent by volume) may be recirculated to the gas processor tube inlet if desired.

The device and method of this invention may be used to continuously extract and concentrate molecules and substances from the flue gases of burner or incinerators such as municipal, industrial or hazardous waste incinerators into a liquid thin film which liquid is subsequently analyzed by wet chemical analytical instrument. The type of liquid used to extract the molecules or substances from the gas sample stream will depend upon what molecules or substances are sought to be extracted. Substances which are readily soluble in water such as acidic substances may be extracted from the sample gas stream by water or by water containing a base such as a hydroxide, an amine or a phosphate. If the gas sample contains substances which are basic in nature, they may be extracted and concentrated by water containing an acid such as phosphoric acid, sulfuric acid, or an organic acid. The acids and bases in the gas sample and in the water may be either Orrehenius or Lewis acids and bases.

In addition to water soluble substances, flue gases may contain hazardous or toxic substances which are not soluble in water such as polynuclear aromatic hydrocarbons and organic pesticides containing sulfur, nitrogen, phosphorous and arsenic, and chlorocarbons. These substances can be continuously extracted and concentrated according to this invention by using solvents such as higher boiling alcohols, gycols, ketones, hydrocarbons and esters. Examples of such solvents which can be used according to this invention are propanol, butanol, isopropanol, octanol, cyelohexanol, ethylene glycol, propylene glycol, glycerol, methyl ethyl ketone, decane, tetrahydronapthalene, dimethyl sulfoxide and sulfolane.

Having generally described the method aspects of the invention and an embodiment of the apparatus used to perform the method of the invention, the following examples are given for the purpose of illustrating the invention and are not to be construed as limiting the invention.

EXAMPLE 1

The exhaust flue of a chemical agent incinerator was simulated using tributylamine (TBA), as a model compound for chemical agents. The simulated flue gas was an air stream containing 39 ppb TBA. The sample processing tube was a 180 inch long, 0.625 inch outer diameter, 0.509 inch inner diameter Teflon tube whose inner surface had been etched by sodium napthenate based etchant (Fluoroetch Fluorocarbon Etchant; Acton Associates, Inc., Pittston, Pa.). The tube was coiled into a 30 inch helix; 30 inches in diameter and was vertically inclined when mounted. The liquid used to wet the inner wall of the tube was deionized water containing from about 175 to about 75 $\mu l/l$ of a surfactant such as IVC (common name BRIJ-35) that has been acidified to about pH 2.3 with phosphoric acid. The TBA analysis was conducted using a Technicon Model 650 colorimetric analyzer. The operating parameters for the test with the etched Teflon tube were:

| A. | Thermal Conditions | |
|---|---|---|
| | Control Temperatures (Tube) | 60° C.–70° C. (range) |
| | Gas Inlet Temp., Max. | 200° C.; −10° C., + 0° C. |
| | Outlet Temp.(Tube), gas and liquid | 60° C.–70° C. (range) |
| B. | Pneumatic/Hydraulic Conditions | |
| | Gas Sample Flow (inlet) | 250–260° 1/min. at 200° C.; 1 atm. |
| | Gas Sample Flow (outlet) | 150–160° 1/min. at 20° C.; 1 atm. |
| | Gas Velocity | 1980 cm/sec. (64 ft./sec.) |
| | Maximum pressure drop | 0.1 psi |
| | Liquid water flow (inlet) | 7–10 ml/min. |
| | Liquid water flow (outlet) | 3–5 ml/min. |

The analysis of the TBA containing effluent gave an extraction efficiency of 57–65 percent. The calculated efficiency for chemical agents (based on the TBA result) is 85 percent and the concentration factor is in the range of about 53,000–71,000. The response time is about 45 seconds from the time of input of contaminated gas, to delivery of the concentrated sample at the instrument outlet.

Chemical agents such as 3-Quinuclidinyl benzilate may be colorimetrically analyzed in a conventional manner in the Technicon Analyzer by combining a portion of the liquid sample stream with chloroform, Xylene Red, B Dye and a buffer solution of 0.1 molar citric acid and 0.2 molar sodium phosphate mixed in a 9:1 ratio.

While the present invention has been particularly described with respect to a particular embodiment described herein, it will be appreciated that various modifications and adaptations may be made based on the present disclosure and which are intended to be within the spirit and scope of the present invention as set forth in the following claims.

What is claimed is:

1. Apparatus for removing and concentrating substances from a flowing sample gas stream and depositing such molecules or substances in a liquid film stream comprising a hollow fluorocarbon cample processing tube having an inlet orifice, and outlet orifice, and outer wall and a hydrophylic inner wall having a cross-sectional area in the range of 0.15 to 0.30 square inches and a length of at least 100 inches;

a top cap having liquid dispersion ports uniformly distributed around the inner circumference of said inlet orifice of said tube whereby a surfactant containing liquid entering into the cap from an external source may be uniformly dispersed from the cap onto said hydrophylic inner wall of the tube where it may uniformly flow, in a thin film manner, from the inlet orifice of the tube to the outlet orifice of the tube, and the top cap also having a gas injection port whereby a gas containing the molecules or substances sought to be removed and concentrated from the flowing sample gas stream can be intruduced into the inlet orifice of the tube and caused to flow through the tube; and a bottom cap at the outlet orifice of the tube, the bottom cap having a liquid collection well with a liquid port whereby the thin film liquid flowing down the inner wall of the tube can be collected and transported to an analyzer, and the bottom cap also having a gas outlet port whereby the flowing sample gas stream undergoing sampling and analysis can be removed from the tube and vented.

2. A sample processing tube in accordance with claim 2, wherein the inner surface of the tube is chemically etched to provide a hydrophilic surface.

3. A method for removing and concentrating substances from a flowing gas sample stream and depositing such substances in a liquid film stream in a controlled and quantitative fashion, the method comprising the steps of:

sampling a flowing gas stream by means of a gas probe inserted in the gas stream and transporting the flowing sample gas stream so obtained through a heated transport line to a gas inlet port in an inlet cap of a heated hollow fluorocarbon sample processing tube having a length of at least 100 inches, and a diameter in the range of 0.35 to 0.625 inches having a hydrophylic inner surface;

dispersing a surfactant containing liquid uniformly and circumferentially on the inner surface of the hollow tube by means of liquid dispersion ports circumferentially placed in the top or inlet cap of the sample processing tube, the surfactant containing liquid having been delivered from a liquid reservoir by means of a liquid transport line, a liquid pump and a liquid metering valve;

removing the substance to be analyzed from the flowing sample gas stream by means of contact of the flowing sample gas stream with the liquid film stream whereby the molecules or substances to be analyzed are removed from the flowing sample gas stream and concentrated in the liquid film stream at the gas-liquid interface to a value such that the concentration of the substance in the liquid film stream is at least 50,000 times the concentration of the substance in the flowing gas stream;

collecting the liquid containing the concentrated substance in a liquid collection well located circumferentially in an outlet cap of the sample processing tube, the liquid collecting well having a liquid port whereby the liquid can be removed from the wall, and venting the flowing sample gas stream from the sample processing tube.

4. A method in accordance with claim 3, wherein the gas transport line is heated to a temperature in the range of about 150° C. to about 300° C.

5. A method in accordance with claim 3, wherein the gas transport line is heated to a temperature in the range of about 175° C. to about 225° C.

6. A method in accordance with claim 3, wherein the hollow tube is heated to a temperature in the range of about 50° C. to about 90° C.

7. A method in accordance with claim 3, wherein the inner surface of the tube is etched by means of a chemically etching agent.

8. A method in accordance with claim 3, wherein the ratio of the gas/liquid inlet flow volumes is in the range of about 8,000:1 to about 15,000:1.

9. A method in accordance with claim 3, wherein the liquid is an ambient temperature liquid selected from the group consisting of water, glycols, alcohols, ketones, esters and hydrocarbons.

10. A method in accordance with claim 3, wherein the liquid is water, ethylene glycol, propylene glycol, propanol, butanol, isopropanol, isobutanol, methyl ethyl ketone, pentanone and tetrahydronapthalene.

11. A method in accordance with claim 3, wherein the liquid is water.

12. A method in accordance with claim 3, wherein the boiling point of the liquid is greater than the temperature of the processing tube by an amount in the range of 20° C. to about 120° C.

13. A method in accordance with claim 3, wherein the surfactant is a nonionic surfactant.

* * * * *

UNITED STATES PATENT AND TRADEMARK OFFICE
CERTIFICATE OF CORRECTION

PATENT NO. : 4,883,505                  Page 1 of 2

DATED : November 28, 1989

INVENTOR(S) : Daniel P. Lucero

It is certified that error appears in the above-identified patent and that said Letters Patent is hereby corrected as shown below:

Column 1, line 14, after "aspect" delete "," (comma).

Column 1, line 59, change "benziloute or "BZ")" to --benzilate) or "BZ"--.

Column 2, line 43, change "absorbent" to "absorbant".

Column 3, line 3, after "to" insert --about--.

Column 3, line 15, change "of" to --or--.

Column 3, line 65, delete "and".

Column 4, lines 54-55, change "lo" to --low--.

Column 5, line 54, change "streeam" to --stream--.

Column 5, line 60, change "ocurrence" to --occurrence--.

Column 6, line 12, after "11" insert --, a--.

Column 6, line 65, change "particules" to --particles--.

UNITED STATES PATENT AND TRADEMARK OFFICE
CERTIFICATE OF CORRECTION

PATENT NO. : 4,883,505
DATED : November 28, 1989
INVENTOR(S) : Daniel P. Lucero

It is certified that error appears in the above-identified patent and that said Letters Patent is hereby corrected as shown below:

Column 7, line 56, change "gycols" to --glycols--.

Column 7, line 59, change "cyelohexanol" to --cyclohexanol--.

Column 8, line 64, change "cample" to --sample--.

Column 9, line 12, change "intruduced" to --introduced--.

Column 9, line 24, change "2" to --1--.

Column 10, line 14, change "wall" to --well--.

Signed and Sealed this

Twenty-second Day of January, 1991

Attest:

HARRY F. MANBECK, JR.

*Attesting Officer*  *Commissioner of Patents and Trademarks*